US007531146B2

(12) United States Patent
Gorval

(10) Patent No.: US 7,531,146 B2
(45) Date of Patent: May 12, 2009

(54) SYNTHESIS FURNACE

(75) Inventor: Evgeni Gorval, Dortmund (DE)

(73) Assignee: UHDE GmbH, Dortmund (DE)

( * ) Notice: Subject to any disclaimer, the term of this patent is extended or adjusted under 35 U.S.C. 154(b) by 400 days.

(21) Appl. No.: 10/581,181

(22) PCT Filed: Oct. 13, 2004

(86) PCT No.: PCT/EP2004/011442

§ 371 (c)(1),
(2), (4) Date: Jun. 1, 2006

(87) PCT Pub. No.: WO2005/053834

PCT Pub. Date: Jun. 16, 2005

(65) Prior Publication Data

US 2007/0128091 A1  Jun. 7, 2007

(30) Foreign Application Priority Data

Dec. 4, 2003   (DE) .................... 103 57 064

(51) Int. Cl.
*B01J 8/04* (2006.01)
*B01J 19/00* (2006.01)
(52) U.S. Cl. .............. 422/197; 422/198; 422/204; 48/127.9
(58) Field of Classification Search .......... 422/197, 422/198, 204; 48/127.9
See application file for complete search history.

(56) References Cited

U.S. PATENT DOCUMENTS

| 2,338,295 A | 1/1944 | Mekler |
| 2,598,879 A | 6/1952 | Barnes |
| 3,257,172 A | 6/1966 | Kao et al. |
| 3,476,519 A | 11/1969 | Decaux |
| 4,405,564 A * | 9/1983 | Herbort et al. .......... 422/197 |
| 4,405,565 A * | 9/1983 | Herbort et al. .......... 422/197 |

OTHER PUBLICATIONS

International Search Report.
Ammonia: Principles and Industrial Practice/Max Appl—Weinheim; New York; Chichester; Brisbane; Singapore; Toronto: Wiley-VCH, 1999, ISBN 3-527-29593-3, pp. 80-89 (to follow).
Fluegas Flow Patterns in Top-fired Steam Reforming Furnaces, P.W. Farnell & W.J. Cotton, Synetix, Billingham, England, 44th Annual Safety in Ammonia Plants and Related Facilities Symposium, Seattle, Washington, Paper No. 3e, Sep. 27-30, 1999) (to follow).

* cited by examiner

*Primary Examiner*—Walter D Griffin
*Assistant Examiner*—Lessanework Seifu
(74) *Attorney, Agent, or Firm*—Collard & Roe, P.C.

(57) ABSTRACT

A synthesis furnace has a furnace chamber surrounded by a circumferential furnace wall, in which burners are disposed essentially in one plane, with burner exit direction directed downward, and reaction tubes are disposed essentially vertically and parallel to one another. The reaction tubes are heated externally by the ignited burners. To improve the heat distribution and the entire heat transfer in as simple a manner as possible, in terms of design and control technology, at least the outer burners disposed in the vicinity of the furnace wall have a burner exit direction that runs at an incline away from the center of the furnace in relation to the vertical.

5 Claims, 4 Drawing Sheets

SYNTHESIS FURNACE

CROSS REFERENCE TO RELATED APPLICATIONS

Figure 1:
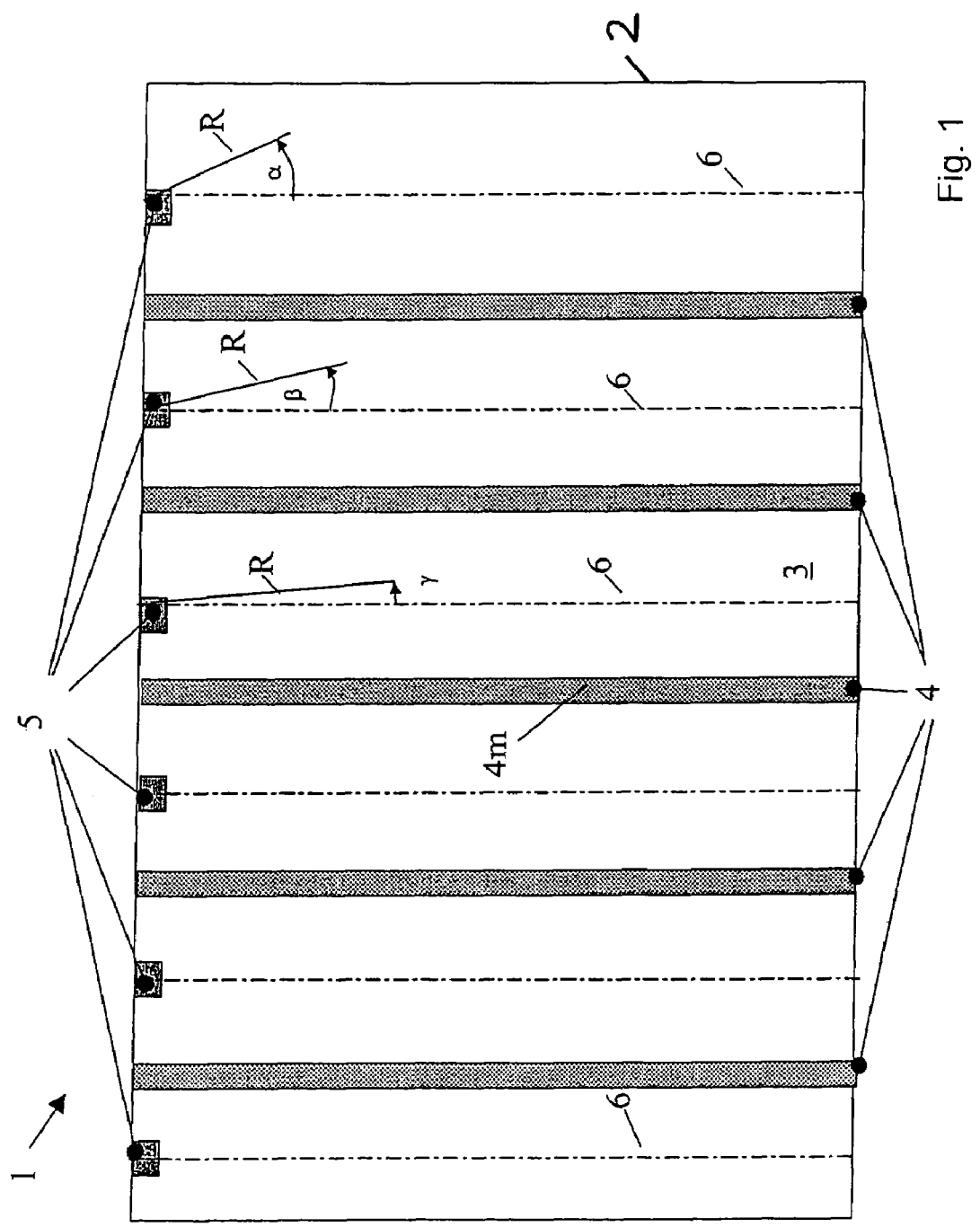

Applicant claims priority under 35 U.S.C. §119 of German Application No. 103 57 064.0 filed Dec. 4, 2003. Applicant also claims priority under 35 U.S.C. §365 of PCT/EP2004/011442 filed Oct. 13, 2004. The international application under PCT article 21(2) was not published in English.

The invention relates to a synthesis furnace having a furnace chamber enclosed by a circumferential furnace wall, in which a plurality of burners, essentially disposed on one plane, having the burner exit direction directed downward, and a plurality of reaction tubes that run essentially vertically and parallel to one another are disposed, whereby the reaction tubes are heated from the outside, by means of the firing burners.

Such synthesis furnaces, e.g. for the production of ammonia, methanol, or hydrogen, are sufficiently known and are frequently configured, for large-scale technical use, as ceiling-fired box furnaces of this type, having reaction/splitting tubes that stand vertically. These splitting tubes are disposed in rows, and the process gas flows through them from top to bottom. In this connection, this process gas is subjected to a so-called splitting process. The process gas is collected at the bottom, inside or outside of the furnace, in exit collectors. In the alleys that lie between the rows of tubes, the tubes are heated by means of the burners disposed in the furnace, which fire vertically downward; in this connection, the flue gas generated by the burners flows through the furnace from top to bottom and is drawn off through gas tunnels disposed at the base (e.g. published in: "Ammonia: Principles and Industrial Practice/Max Appl—Weinheim; N.Y.; Chichester; Brisbane; Singapore; Toronto: Wiley-VCH, 1999, ISBN 3-527-29593-3, pages 80-89).

In such synthesis furnaces, particularly those having a plurality of rows of pipes, a very non-uniform flow, particularly in the outer rows of pipes, especially determined by re-circulation, is observed. This re-circulation results in low flue gas and process gas temperatures in the outer rows of pipes, in comparison with the middle rows. This low temperature in the outer rows has a detrimental effect on the splitting process. Furthermore, flame deflection occurs in the outer burner rows, and this worsens the entire heat transfer and increases the material stress.

Various solution paths have already been proposed to avoid these known problems (Fluegas Flow Patterns in Top-fired Steam Reforming Furnaces, P. W. Farnell & W. J. Cotton, Synetix, Billingham, England, 44th Annual Safety in Ammonia Plants and Related Facilities Symposium, Seattle, Wash., Paper No. 3e, Sep. 27-30, 1999). Thus it has been proposed, for one thing, to operate the outer burners at higher air exit speeds, and for another, to distribute the process gas among the reaction tubes in different amounts, in targeted manner. However, these two solutions have not proven to be satisfactory. Furthermore, it has been proposed to increase the distance between the burners and the furnace wall. However, this solution does not eliminate the problems described above, either.

It is therefore the task of the invention to improve the heat distribution and the entire heat transfer in as simple a manner as possible, in terms of design and control technology.

This task is accomplished, in the case of a synthesis furnace of the type described initially, according to the invention, in that at least the outer burners, disposed in the region of the furnace wall, have a burner exit direction that is inclined relative to the vertical, leading away from the center of the furnace.

It has turned out that by means of this solution path, which is completely different as compared with the known solution paths described above, the flame deflection of the outer burner rows towards the center of the furnace can be clearly reduced, in a manner that is simple in terms of design and control technology. A significantly more uniform flow-off of the flue gases along the reaction tubes occurs, the heat transfer is improved, and the increased material stress on the reaction tubes due to "hot spots" in the case of synthesis furnaces according to the state of the art is clearly reduced, so that the lifetime of the reaction tubes clearly increases.

In order to achieve particularly good heat distribution and/or flue gas flow, it is preferably provided that the incline of the burner exit directions of the individual burners is different. This means that the burners are disposed in a corresponding incline angle (opposite to the suction effect of adjacent burners) that is dependent on the suction effect of adjacent burner flames on the burner's own flame.

In this connection, it is very particularly preferably provided that the incline of the burner exit directions of the burners increases towards the outside towards the furnace wall, proceeding from the center of the furnace. While the burners disposed in the center have no incline, for example, the incline of the burner rows then increases towards the outside, to a maximal value.

It has proven to be particularly practical that the incline angle, proceeding from the center, lies between 0 and 10°, preferably between 0 and 5°.

In order to implement the incline of the burners, it can be preferred, in terms of design, that the burners having an inclined burner exit direction are installed to be inclined overall, and/or that their burner opening is disposed at an incline.

It is very particularly preferably provided that the incline of the burner exit directions is adjustable, i.e. this can be changed during operation of the synthesis furnace, to adapt to the conditions, in each instance.

For this purpose, it is very particularly preferably provided that a control that takes the operating parameters of the synthesis furnace into account is provided to adjust the inclines.

Figure 2A:
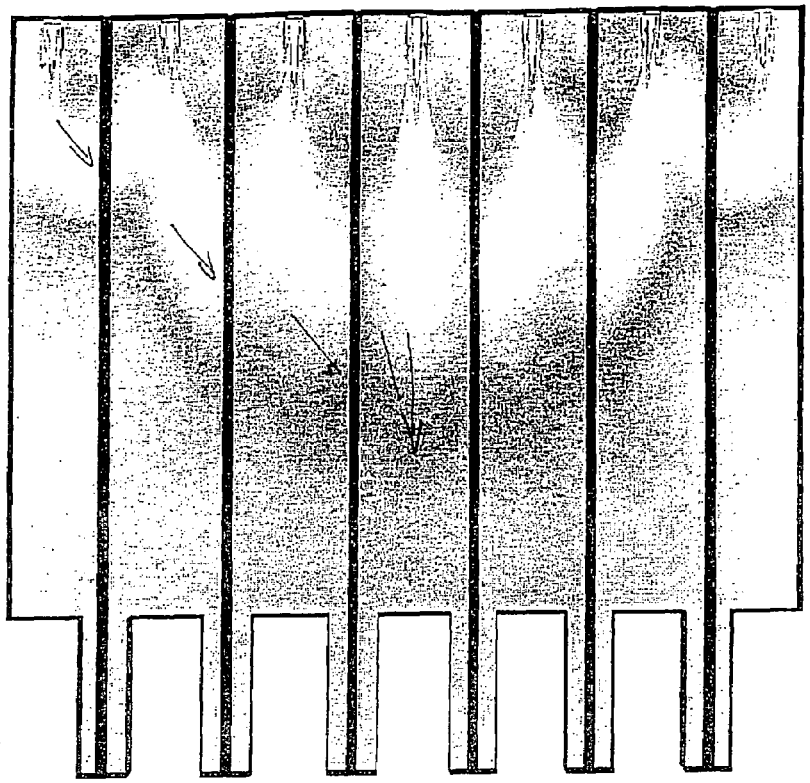
Figure 2B:
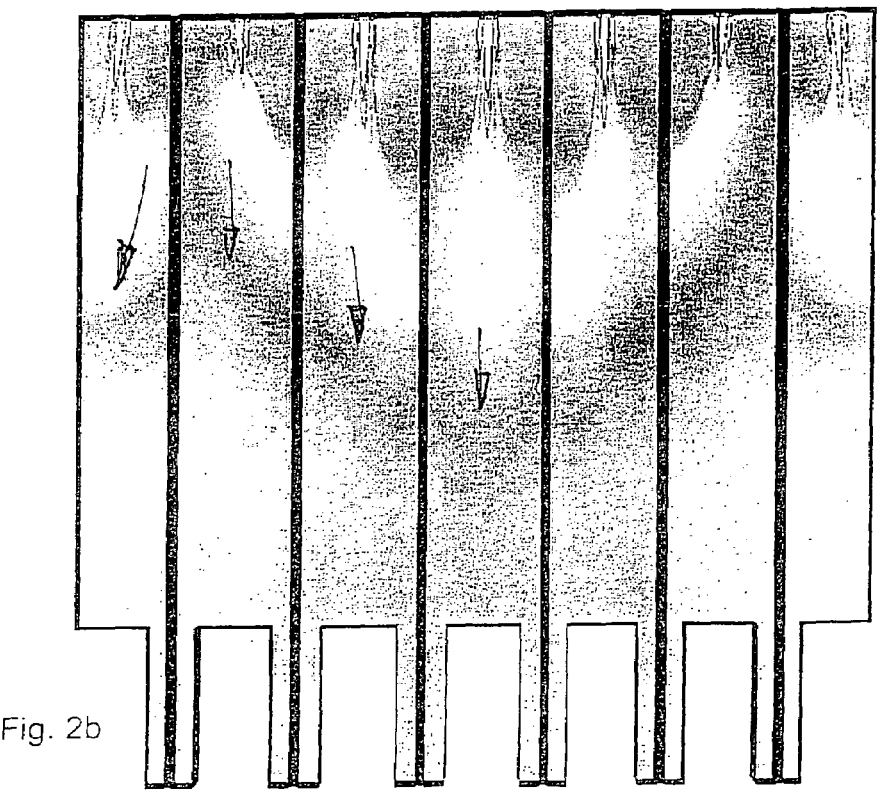
Figure 3A:
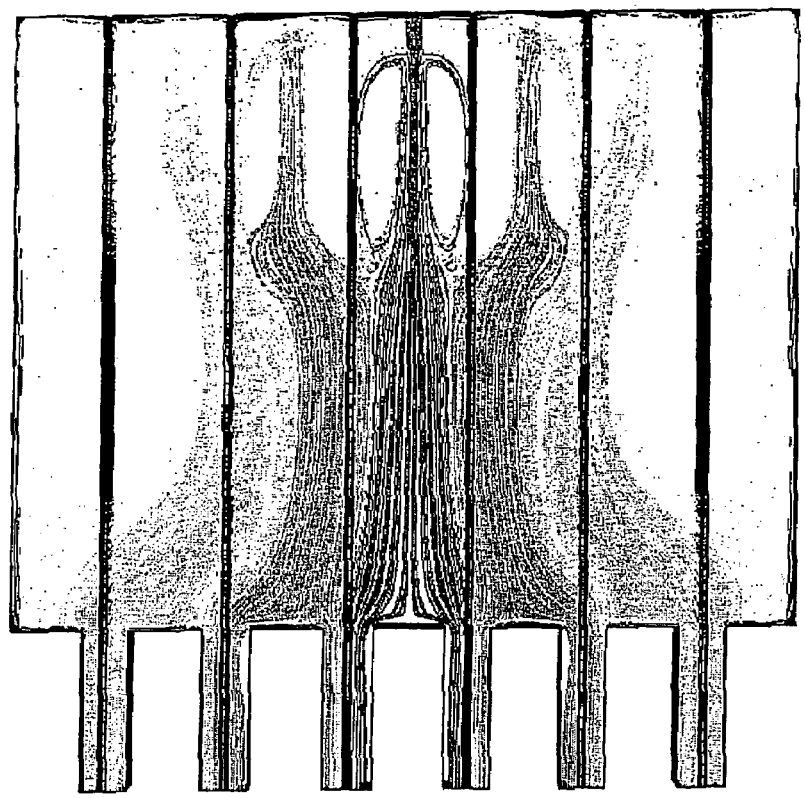
Figure 3B:
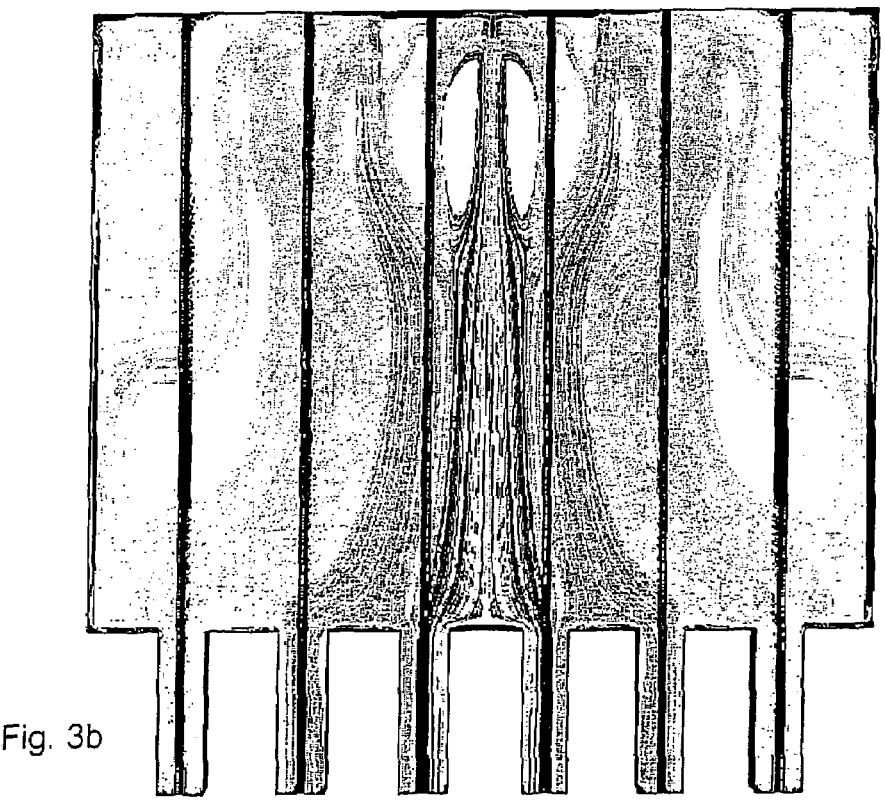
Figure 4:
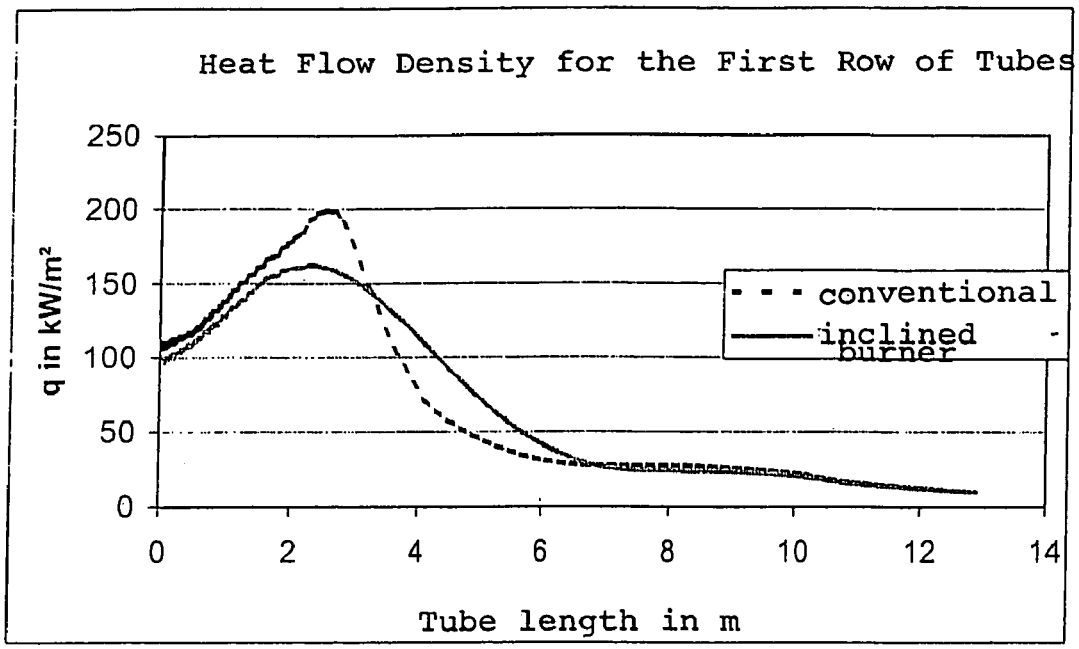

The invention is described in greater detail in the following, using the drawing, as an example. The drawing shows:

FIG. 1 a fundamental diagram of a synthesis furnace,

FIG. 2a the temperature distribution in a synthesis furnace according to the state of the art, FIG. 2b the temperature distribution in a synthesis furnace according to the invention, FIG. 3a flow lines in a synthesis furnace according to the state of the art, FIG. 3b flow lines in a synthesis furnace according to the invention, and FIG. 4 a diagram in which the heat flow density for the outermost row of tubes is shown over the tube length, for a synthesis furnace according to the state of the art and a synthesis furnace according to the invention.

A synthesis furnace is referred to in general as 1 in FIG. 1. This synthesis furnace is structured in box shape, i.e. block shape, and has a furnace chamber 3 enclosed by a circumferential furnace wall 2.

Within this furnace chamber 3, a plurality of reaction tubes 4 that run essentially vertically and parallel to one another are disposed, through which process gas is introduced from the top, which is not shown in greater detail. This process gas flows through the reaction tubes 4 from the top to the bottom, and is collected in exit collectors, not shown, in the bottom region of the furnace and/or outside of same.

In the region between the reaction tubes 4 and/or rows of tubes formed by them, a plurality of burners 5 are disposed in the upper region of the furnace chamber 3, essentially in one plane. These burners 5 have a burner exit direction that is directed downward, in each instance; in FIG. 1, a vertical burner axis 6 is drawn with a dot-dash line for each burner 5.

It is now significant that at least the outer burners 5, disposed in the region of the furnace wall 2, have a burner exit direction R that is inclined relative to the vertical, leading away from the center of the synthesis furnace 1. This incline angle is designated as $\alpha$ in FIG. 1 and defined relative to the related vertical burner axis 6. It is obvious that this incline can also or additionally extend in the plane extended transverse to the plane of the drawing, as shown, relative to the center of the furnace chamber 3, differing from the two-dimensional representation according to FIG. 1, depending on the arrangement of the burners. In this connection, the center of the furnace chamber 3 is located in the region of the plane that accommodates the middle reaction tubes 4m.

It is particularly practical if not only the burner exit directions R of the outer burners 5 are inclined, but also of the middle and inner burners, whereby the arrangement is then made in such a manner that the incline increases, proceeding from the inner burners to the furnace wall 2; it is evident that the incline $\gamma$ of the inner burners is smaller than the incline $\beta$ of the middle burners, and this again is smaller than the incline $\alpha$ of the outer burners.

The incline angles $\alpha$ of the outer burners lie approximately maximally at 10°, preferably at 5°; the incline angles $\beta$ and $\gamma$ are suitably selected to be smaller.

The incline of the burners 5 can be implemented in different ways; it can be provided, on the one hand, that the burners are installed inclined as a whole, or only their burner opening, i.e. burner jet.

It is particularly practical if the incline of the burners 5 is configured to be adjustable, particularly also during operation; in this case, a control, not shown, can be provided for the synthesis furnace 1, which undertakes an adjustment of the incline, taking into consideration the operating parameters of the synthesis furnace 1.

The flame deflection of the outer burner rows towards the center is clearly reduced by means of this configuration of the burners 5; a uniform or more uniform flow-off of the flue gas along the reaction tubes occurs, the heat transfer is improved, and the increased material stress due to "hot spots" is clearly reduced. These advantages as compared with the state of the art are clearly evident from FIGS. 2a, 2b, on the one hand, and 3a, 3b, on the other hand.

FIG. 2a shows a very non-uniform temperature distribution in the case of a conventional synthesis furnace without burner incline. In comparison, a configuration according to the invention can be seen in FIG. 2b, in which the outer burners, i.e. their burner exit direction, is inclined by 5°; a significantly more homogeneous temperature distribution occurs.

The situation is similar for the flow conditions that are shown in FIGS. 3a and 3b. FIG. 3a shows the flow conditions in the case of a conventional synthesis furnace without burner incline, and FIG. 3b with burner incline, specifically by 5° in the case of the outer burners. The undesirable dead zones (white empty areas) are clearly reduced in the case of the configuration according to the invention.

In FIG. 4, the heat flow density for the outermost row of tubes is plotted over the tube length, specifically with a broken line for a synthesis furnace according to the state of the art, and with a solid line for a synthesis furnace according to the invention, having outer burners inclined by 5°. It is evident that the heat flow density over the tube length is distributed significantly more uniformly in the case of a synthesis furnace according to the invention.

The invention claimed is:

1. Synthesis furnace (1) having a furnace chamber (3) surrounded by a circumferential furnace wall (2), in which a plurality of burners (5) disposed essentially in one plane, with burner exit direction directed downward, whereby at least the outer burners (5) disposed in the region of the furnace wall (2) have a burner exit direction (R) that is inclined relative to the vertical, leading away from the center of the furnace, and in which a plurality of reaction tubes (4) disposed essentially vertically and parallel to one another are disposed, the reaction tubes being heated from the outside, by means of the firing burners (5), wherein the incline of the burner exit directions (R) of the individual burner rows is different, and wherein the incline of the burner exit directions (R) of the burner rows increases toward the outside, toward the furnace wall (2), proceeding from the center of the furnace.

2. Synthesis furnace according to claim 1, wherein the incline angle, proceeding from the center of the furnace, lies between 0 and 10°.

3. Synthesis furnace according to claim 1, wherein the burners (5) are installed with inclined burner exit direction (R), in total, and/or their burner exit opening is disposed at an incline.

4. Synthesis furnace according to claim 3, wherein the incline of the burner exit directions (R) is adjustable.

5. Synthesis furnace according to claim 4, further comprising a control device that takes the operating parameters of the synthesis furnace into account for adjusting the inclines.

* * * * *